United States Patent [19]

LaPlante

[11] Patent Number: 4,975,055

[45] Date of Patent: Dec. 4, 1990

[54] FLEXIBLE CONDUIT STRUCTURE FOR DENTAL APPLIANCES

[75] Inventor: Pierre LaPlante, Newberg, Oreg.

[73] Assignee: A-Dec, Inc., Newberg, Oreg.

[21] Appl. No.: 318,823

[22] Filed: Mar. 2, 1989

[51] Int. Cl.$^5$ .............................................. A61C 17/02
[52] U.S. Cl. ...................................... 433/82; 138/111; 138/115; 285/137.1
[58] Field of Search ......................... 138/111, 113, 115; 433/141, 80, 82, 84; 285/131, 137.1

[56] References Cited

U.S. PATENT DOCUMENTS

| | | | |
|---|---|---|---|
| 2,908,949 | 10/1959 | Frehse | 138/111 |
| 3,004,330 | 10/1961 | Wilkins | 138/115 |
| 3,061,930 | 11/1962 | Borden | 433/82 |
| 3,612,352 | 10/1971 | Smith | 433/80 |
| 3,952,416 | 4/1976 | Lingenhöle | 433/82 |
| 4,176,453 | 12/1979 | Abbott | 433/82 |
| 4,531,913 | 7/1985 | Taguchi | 433/80 |
| 4,729,409 | 3/1988 | Paul | 138/115 |
| 4,872,837 | 10/1989 | Issalane et al. | 433/80 |

FOREIGN PATENT DOCUMENTS

| | | | |
|---|---|---|---|
| 0160498 | 11/1985 | European Pat. Off. | 138/115 |
| 0707396 | 5/1941 | Fed. Rep. of Germany | 138/111 |
| 8005762 | 4/1981 | Netherlands | 138/115 |

*Primary Examiner*—James E. Bryant, III
*Attorney, Agent, or Firm*—Klarquist, Sparkman, Campbell, Leigh & Whinston

[57] ABSTRACT

An extruded conduit structure for conveying several different fluids is provided comprising a cluster of at least three tubes connected by webs extending between adjacent pairs, the tubes and webs being formed by simultaneous extrusion of a suitable plastic through a suitable die. The outer surface of each of the webs is convexly curved in an arc that is substantially tangential with the outer surfaces of the adjacent pair of tubes. The inner surface of each of the webs is flat relative to the outer surface and forms a cord of such arc whereby each of the webs will be of minimum thickness along each of its junctures with the adjacent webs. This construction substantially eliminates any concave surfaces on the exterior of the conduit within which foreign matter may collect and, because of the thinner wall sections at the juncture of the webs with the adjacent tubes, the webs can be easily stripped along the tubes to expose the tube ends for connection to the appartus, such as a dental handpiece to which they are to be connected.

8 Claims, 1 Drawing Sheet

HANDPIECE

FLEXIBLE CONDUIT STRUCTURE FOR DENTAL APPLIANCES

The present invention relates to a conduit structure and more particularly, to a flexible conduit structure comprised of a plurality of tubes for conveying a plurality of fluids to dental handpieces or the like.

BACKGROUND OF THE INVENTION

Certain medical and dental appliances, such as dental handpieces, require the supply of multiple fluids during their operation. For example, a dental handpiece may require air to be supplied under pressure to drive the turbine by which the dental burr or other tool is driven. The dental handpiece may also be provided with outlets for projection of cooling air and/or water upon a tooth as it is being abraded by a dental burr driven by the handpiece. In the case of the drive air, the exhaust air is sometimes conveyed out of the mouth rather than being exhausted from the turbine directly into the mouth. These fluids have been conveyed to and from the mouth in flexible tubes and, for convenience of handling and appearance, the tubes have been bundled together. It is also commonplace to form such bundles by extruding a plurality of tubes connected by webs of the extruded material. As provided heretofore, such webs provided a concave surface between adjacent pairs of tubes which is undesirable in that foreign matter may deposit therein.

It is, therefore, an object of the present invention to provide a new and improved conduit structure for conveying a multiple number of fluids to a medical or dental appliance.

More particularly, it is an object of the present invention to provide a conduit structure which is substantially free of indentations on its exterior surface in which foreign matter can collect.

Still another object of the invention is to provide a conduit structure comprising multiple tubes connected by webs wherein the webs are of lesser thickness along their juncture with each of the adjacent tubes whereby the webs may be stripped from such tubes easily and cleanly.

Other objects and advantages of the invention will become more apparent hereinafter.

SUMMARY OF THE INVENTION

In accordance with a preferred embodiment of the invention, an extruded conduit structure is provided comprising a cluster of at least three tubes connected by webs extending between adjacent pairs, the tubes and webs being formed by simultaneous extrusion of a suitable plastic through a suitable die. The outer surface of each of the webs is convexly curved in an arc that is substantially tangential with the outer surfaces of the adjacent pair of tubes. The inner surface of each of the webs is flat relative to the outer surface and forms a cord of such arc whereby each of the webs will be of minimum thickness along each of its junctures with the adjacent webs. This construction substantially eliminates any concave surfaces on the exterior of the conduit within which foreign matter may collect and, because of the thinner wall sections at the juncture of the webs with the adjacent tubes, the webs can be easily stripped along the tubes to expose the tube ends for connection to the apparatus to which they are to be connected.

DETAILED DESCRIPTION OF THE INVENTION

Figure 1:
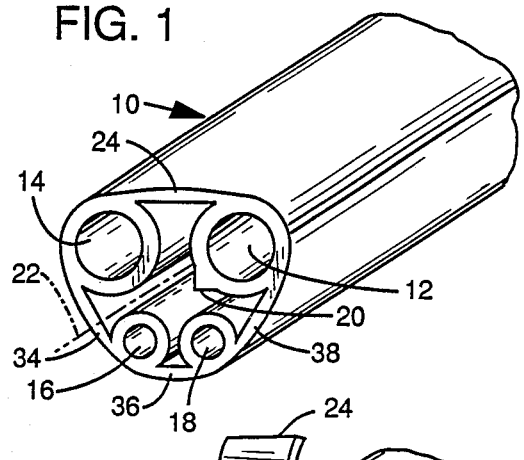
FIG. 1 is a perspective view of a conduit structure constructed in accordance with the present invention and containing four tubes.
Figure 2:
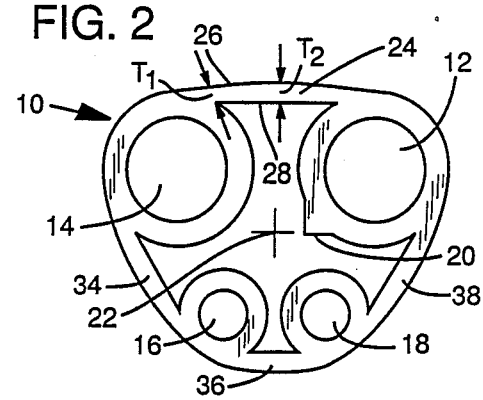
FIG. 2 is an enlarged cross-sectional view of the conduit structure of FIG. 1.

Referring to FIGS. 1 and 2, therein is illustrated a length of conduit structure 10 constructed in accordance with the invention for use with a dental handpiece and comprising wall means defining four tubes 12, 14, 16 and 18. Tubes 12 and 14 are of larger diameter than tubes 16 and 18. Tube 12 is formed with an identifying rib 20 along the length thereof and, in accordance with custom, is utilized to convey drive air to a dental handpiece. The tube 14 is provided for conducting the exhaust drive air away from the dental handpiece so that it may be exhausted at some remote location. The tubes 16, 18 are provided for conveying air and water, respectively, to the dental handpiece for the purposes of cooling the work area in the tooth of a patient. The conduit structure 10 is formed by extrusion of a suitable extrudable material such as polyvinyl chloride or polyurethane.

The tubes 12 and 14 are connected by a web 24, the outer surface 26 of which is convexly curved preferably on an arc such that its intersection with a plane perpendicular to the axis 22 of the conduit structure 10 defines an arc which is substantially tangential with the outer surfaces of the tubes 12, 14. The web 24 preferably is thinnest adjacent each of the tubes 12, 14. In a preferred embodiment of the invention, the inner surface 28 of the web 24 is such that it intersects a plane perpendicular to the axis 22 along a cord of the arc 26, the line of intersection being substantially perpendicular to a radius of the arc defining the outer surface 26 substantially at the midpoint of the web. With this construction, the web will have a minimum thickness $T_1$ at its juncture with adjacent tubes 12, 14 and a maximum thickness $T_2$ at its midpoint.

Figure 3:
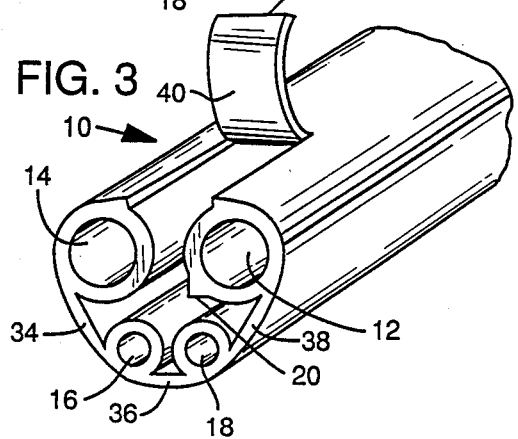
FIG. 3 is a perspective view of the conduit structure of FIG. 1 illustrating how the web between tubes can be peeled back.

Similarly, the tubes 14, 16 are connected by a web 34, the tubes 16, 18 by a web 36, and the tubes 12, 18 by a web 38. Each of the webs 34, 36, 38 is formed preferably in the same manner as the web 24, i.e., with a convex outer surface that is tangential with the surfaces of the adjacent pairs of tubes and with an inner surface that is flat such that the intersection of the corresponding web with the adjacent tubes is thinnest along the juncture of the web with the tubes adjacent thereto. The construction of the webs whereby they are thinner along their juncture points with the adjacent tubes, permits the webs to be peeled back as indicated in FIG. 3, where a peeled back portion 40 of the web 24 is illustrated, so as to expose the ends of the adjacent tubes 12, 14. Likewise, the similar portions of the webs 34, 36 and 38 could be peeled back and thereafter all of the web ends cut off leaving the ends of the tubes exposed so that they may more conveniently be slipped onto the cooperative fittings of a dental handpiece or the like.

Figure 5:
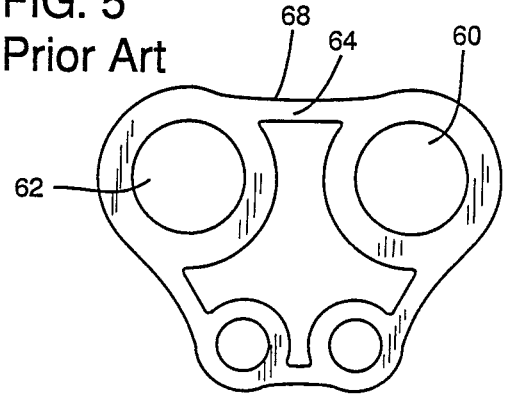
FIG. 5 is an end view of a conduit structure made in accordance with the prior art.

The provision of the convex surfaces, such as the surface 26, on connecting webs 24, 34, 36 and 38 of the conduit structure, substantially reduces or eliminates the presence of concave surfaces along the exterior of the conduit structure within which foreign matter may collect. Such foreign matter may include undesirable bacteria of infectious diseases. In FIG. 5, for example, there is shown in cross-section a prior art conduit structure of which I am aware for use with a dental handpiece comprising four tubes, including a tube 60 for drive air and a tube 62 for exhaust air and which tubes are connected by a web 64 which is of substantially uniform thickness between the tubes 62, 64 and the outer surface 68 of which was concavely curved between the tubes 62, 64 so as to provide a substantial indentation of about 0.020 inches at its center extending along the length of the conduit structure and in which foreign matter could collect. The indentations between the other pairs of tubes ranged from 0.006 to 0.016 inches.

Figure 4:
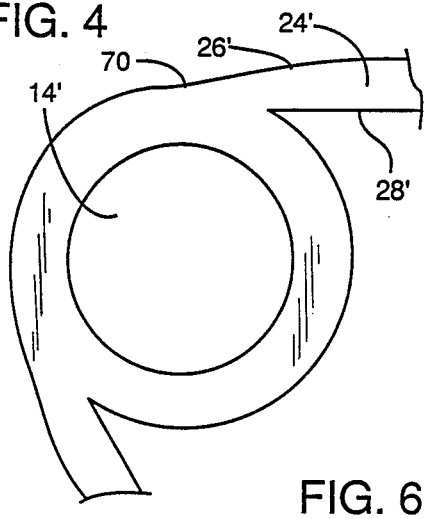
FIG. 4 is an enlarged fragmentary end view of a conduit structure made in accordance with the invention.

As a practical matter, it is sometimes impossible to extrude a tube with the exact desired configuration as is shown in FIG. 2. For example, in FIG. 4, there is shown an enlarged end portion of a conduit structure including a tube 14' and a convex web 24' wherein the convex outer surface 26' is not quite tangential with the outer surface of the tube 14', thus forming a slight indentation 70 which would extend along the length of the tube and in which some foreign matter might conceivably collect. These I have observed to be only between 0.003 and 0.007 inches deep. However, indentations of such depth have a much smaller volume than the indentations in the prior art structure of FIG. 5, so as to collect less foreign material and because they are shallower are much more easily cleaned and, thus, present much less of a health hazard.

Figure 6:
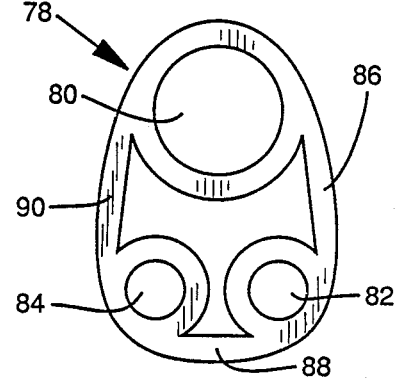
FIG. 6 is an enlarged cross-sectional view of a conduit structure having three tubes and constructed in accordance with the present invention.
Figure 7:
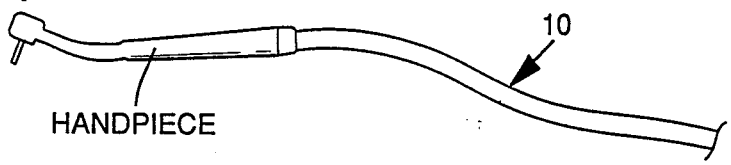
FIG. 7 is a view showing the conduit structure connected to a dental handpiece.

Turning now to FIG. 6, there is shown therein a conduit structure 78 made in accordance with the invention consisting of three tubes and connecting webs including a large tube 80 which may be used for conveying, for example, drive air to a handpiece and two smaller tubes 82, 84 for conveying coolant water and coolant air, respectively, to a handpiece. The tubes 80, 82 are connected by a web 86, the tubes 82, 84 by a web 88, and the tubes 80, 84 by a web 90. Each of such webs is formed with an arcuate convex outer surface that is substantially tangential to the adjacent pairs of tubes so as to avoid the creation of indentations on the outer surface of the conduit, and with an inner surface preferably flat and chordal to the arc of the web outer surface so that the webs are each thinner adjacent the adjacent tubes in the same manner as the embodiment of FIGS. 1 to 4.

As indicated above, the conduit structure of the invention is adapted to be formed by extruding a suitable thermoplastic material through a die which, as will be known to those skilled in the art, will have a configuration substantially complementary to the configuration of the conduit structure. In accordance with conventional practice, the hot, extruded structure will be rapidly cooled by immersing it in water. As the structure is extruded it is preferred that air be blown into the center of the structure so as to maintain a small positive pressure of about five pounds per square inch so as to maintain the webs in a distended configuration as shown in the drawings in FIGS. 1-4 and 6 and prevent their collapsing inwardly as in the prior art structures as shown in FIG. 5.

Having illustrated and described the preferred embodiments of the present invention, it will be apparent that the invention can be modified in arrangement and detail. I claim all such modifications as come within the ambit of the attached claims.

I claim:

1. In combination, a dental handpiece and an extruded conduit structure for conveying air and water to and from said handpiece, said conduit structure comprising:

flexible tubular walls defining a plurality of at least three spaced apart parallel tubes arranged in a cluster and a plurality of webs extending one between each adjacent pair of said tubes and merging with the walls of such tubes to define connected circumferentially extending convex surfaces around the conduit, the outer surface of each of said webs being convexly curved between its juncture with an adjacent pair of tubes, said conduit structure being sufficiently flexible that movement of said dental handpiece is not substantially impaired.

2. A conduit structure as in claim 1 wherein each of said webs is of maximum thickness substantially at its midpoint and of lesser thickness at its juncture with each of the adjacent tubes.

3. A conduit structure as set forth in claim 2 comprising three tubes.

4. A conduit structure as set forth in claim 2 comprising four tubes.

5. An extruded conduit structure as set forth in claim 1 wherein the outer surface of each of said webs is convexly curved such that its intersection with a plane perpendicular to the axis of said conduit structure defines an arc tangential with the outer surfaces of the adjacent pair of tubes with which such web connects.

6. The conduit structure of claim 5, the inner surface of each of said webs being such that it intersects such plane along a chord of such arc and the line of intersection is substantially perpendicular to a radius of such arc intersecting such web substantially at its midpoint.

7. The conduit structure of claim 6 comprising three tubes.

8. The conduit structure of claim 6 comprising four tubes.

* * * * *